United States Patent
Nam et al.

(10) Patent No.: US 9,489,921 B2
(45) Date of Patent: Nov. 8, 2016

(54) METHOD AND APPARATUS FOR DISPLAYING PLURALITY OF DIFFERENT IMAGES OF OBJECT

(71) Applicant: SAMSUNG MEDISON CO., LTD., Hongcheon-gun, Gangwon-do (KR)

(72) Inventors: Ki-Bo Nam, Gangwon-do (KR); Gil-Ju Jin, Gangwon-do (KR)

(73) Assignee: Samsung Medison Co., Ltd., Hongcheon-gun, Gangwon-do (KR)

( * ) Notice: Subject to any disclaimer, the term of this patent is extended or adjusted under 35 U.S.C. 154(b) by 142 days.

(21) Appl. No.: 14/505,193

(22) Filed: Oct. 2, 2014

(65) Prior Publication Data

US 2015/0262553 A1   Sep. 17, 2015

(30) Foreign Application Priority Data

Mar. 12, 2014 (KR) .................. 10-2014-0029269

(51) Int. Cl.
| | |
|---|---|
| G09G 5/14 | (2006.01) |
| A61B 8/00 | (2006.01) |
| G01S 7/52 | (2006.01) |
| G06K 9/32 | (2006.01) |
| G06T 11/60 | (2006.01) |

(52) U.S. Cl.
CPC .............. *G09G 5/14* (2013.01); *A61B 8/463* (2013.01); *A61B 8/467* (2013.01); *A61B 8/469* (2013.01); *G01S 7/52063* (2013.01); *G01S 7/52074* (2013.01); *G06K 9/3233* (2013.01); *G06T 11/60* (2013.01); *G06T 2210/41* (2013.01)

(58) Field of Classification Search
None
See application file for complete search history.

(56) References Cited

U.S. PATENT DOCUMENTS

| | | | |
|---|---|---|---|
| 6,368,277 B1 | 4/2002 | Mao et al. | |
| 6,413,217 B1* | 7/2002 | Mo ................ | G01S 7/52034 600/440 |
| 6,558,324 B1 | 5/2003 | Von Behren et al. | |
| 8,285,357 B2 | 10/2012 | Gardner et al. | |
| 8,471,866 B2 | 6/2013 | Friedman et al. | |
| 2005/0283078 A1* | 12/2005 | Steen ................. | A61B 8/06 600/447 |
| 2010/0106017 A1 | 4/2010 | Shin et al. | |
| 2011/0046487 A1 | 2/2011 | Shin et al. | |
| 2011/0098563 A1 | 4/2011 | Osaka | |
| 2014/0005549 A1* | 1/2014 | Hashimoto ........ | A61B 8/461 600/458 |

FOREIGN PATENT DOCUMENTS

| | | |
|---|---|---|
| EP | 1 529 491 A1 | 5/2005 |
| EP | 2 221 633 A1 | 8/2010 |
| KR | 2011-0019579 A | 2/2011 |
| WO | 2012/176837 A1 | 12/2012 |

OTHER PUBLICATIONS

European Search Report issued in application No. EP 14 182 595.0 dated Jul. 29, 2015.

* cited by examiner

*Primary Examiner* — Maurice L McDowell, Jr.
(74) *Attorney, Agent, or Firm* — McDermott Will & Emery LLP (57) ABSTRACT

Provided is a method of displaying a plurality of different images of an object, the method including displaying a first image produced with respect to the object; selecting at least one region of interest (ROI) from a displayed first image obtained therefrom; producing at least one second image of different type with respect to a selected region of interest; and displaying a first image and the at least one second image.

15 Claims, 6 Drawing Sheets

METHOD AND APPARATUS FOR DISPLAYING PLURALITY OF DIFFERENT IMAGES OF OBJECT

RELATED APPLICATION

This application claims the benefit of Korean Patent Application No. 10-2014-0029269 filed on Mar. 12, 2014, in the Korean Intellectual Property Office, the disclosure of which is incorporated herein in its entirety by reference.

BACKGROUND

1. Field

One or more embodiments of the present invention relate to a method and apparatus for displaying a plurality of different images of an object, and more particularly to a method and apparatus for displaying different images by producing at least one type of image that is related to a selected region of interest of a first image of the object.

2. Description of the Related Art

An ultrasound diagnostic apparatus transmits an ultrasound signal to a predetermined portion of a body, uses reflected ultrasound signal from tissues of the body to obtain images related to layers of soft tissues and blood flow.

In other words, the ultrasound diagnostic apparatus irradiates ultrasound signals generated from a transducer to an object and receives echo signals reflected from the object to obtain images related to internal areas of the object. The ultrasound diagnostic apparatus is advantageous in that information about the object may be displayed in real time. Also, the ultrasound diagnostic apparatus is considered to be safe because there is no X-ray exposure or the like and thus, the ultrasound diagnostic apparatus is widely used with another image diagnostic apparatus such as an X-ray diagnostic device, a computerized tomography scanner, a magnetic resonance image (MRI) apparatus, and a nuclear medicine diagnostic apparatus.

SUMMARY

One or more embodiments of the present invention include a method of displaying a plurality of different images of an object.

Additional aspects will be set forth in part in the description which follows and, in part, will be apparent from the description, or may be learned by practice of the presented embodiments.

According to one or more embodiments of the present invention, provided is a method of displaying a plurality of different images of an object, the method including: displaying a first image produced with respect to the object;

selecting at least one region of interest from the displayed first image obtained therefrom;

producing at least one second image of a type different from a type of the first image, with respect to a selected region of interest; and displaying the first image and the produced at least one second image.

The first image may include a B mode image, and the at least one second image comprises a functional image or a parametric image of the object.

A type of the at least one second image may be preset or determined in real-time based on a frequency of use of each image, reliability of each image during a diagnosis of a lesion, or an external input.

A sequence of displaying the at least one second image with the first image may be preset or determined in real-time based on a frequency of use of each image, reliability of each image during the diagnosis of a lesion, or an external input.

The displaying the first image and the at least one second image may further include overlaying the at least one second image on the region of interest according to an external input to display the same or dispose the second image near the first image to be displayed in parallel.

The method may further include:

selecting at least one sub-region of interest from the displayed at least one second image, extracting a predetermined diagnosis value from a selected sub-region of interest obtained therefrom, and displaying an extracted value obtained therefrom.

When a plurality of regions of interest comprising a first region of interest and a second region of interest in the first image are selected, a type of a second image produced with respect to the first ROI and a type of a second image produced with respect to the second ROI may be the same or different An apparatus for displaying a plurality of different images of an object, the apparatus including:

an image producing unit producing a first image of the object, a display unit displaying the first image produced therefrom, and a region of interest selection unit selecting at least one region of interest selected from at least one first image displayed therefrom, wherein at least one second image of a type different from a type of the first image, with respect to the selected region of interest is produced by the image producing unit, and the first image and the at least two different types of second images are displayed by the display unit.

The first image may include a B mode image and the second image may include a functional image or a parametric image of the object.

A type of the second image may be preset or determined in real-time based on a frequency of use of each image, reliability of each image in diagnosis of a lesion, or an external input.

A sequence of display of at least one second image to be displayed with the first image may be preset or determined in real-time based on a frequency of use of each image, reliability of each image in diagnosis of a lesion, or an external input.

The display unit may overlay the second image on the region of interest according to an external input to display the same or dispose the second image near the first image in parallel.

The apparatus may further include a diagnosis value extraction unit extracting a predetermined diagnosis value from a selected sub-region of interest when at least one sub-region of interest is selected in a displayed second image by a region of interest selection unit, wherein the diagnosis value extracted by the display unit is displayed.

When a plurality of regions of interest including the first region of interest and the second region of interest are selected in the first image, a type of a second image produced for the first region of interest and a type of a second image produced for the second region of interest may be the same or different.

Meanwhile, as an embodiment of the present invention, provided is a computer-readable recording medium, wherein a program for processing any of the program is recorded.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

Terms as used herein will be briefly described and the present invention will be described in greater detail.

The terms as used herein are general terms that are currently being used widely in consideration of functions of the present invention, but the terms may vary depending on the intention of a person in the art or precedents, and the appearance of new technology. Also, in certain cases, an applicant may have randomly selected the terms, in which case, the definitions thereof will be described in detail in the detailed description of the invention. Accordingly, the terms used herein should be defined based on the definitions of the terms and the entirety of the present invention, instead of simple names of the terms.

Throughout the specification, when a portion "includes" a component, another element may be further included, rather than excluding the existence of the other element, unless otherwise described. Also, throughout the specification, terms such as " . . . portion" or "module" refers to a unit for processing at least one function or operation, which may be achieved through hardware, software, or a combination of hardware and software.

Throughout the specification, the expression "ultrasound image" refers to an image of an object obtained by using ultrasound.

The term "object" may refer to a portion of a body. For example, the object may include an organ such as a liver, a heart, a uterus, a brain, a breast, and an abdomen, or a fetus. Also, the object may include a phantom, wherein the phantom may refer to a material that mimics density and acoustic characteristics of human or animal tissues, such as sound velocity and attenuation.

Also, throughout the specification, the term "user" may be a medical professional such as a doctor, a nurse, a medical technologist, a medical imaging specialist, or the like, or a technologist for repairing medical apparatuses, but the medical professional is not limited thereto.

According to conventional technology, different types of images, such as attenuation, sound velocity, shear wave velocity, shear modulus, power doppler, and 3D volume images, are processed and generated through different modes to obtain the images and thus, a mutual comparison thereof is not easy.

In contrast, according to an embodiment of the present invention, all functional images and parametric images may be generated and then displayed, which may be obtained through one scanning of a region of interest of an object without changing the location of a probe. Also, according to an embodiment of the present invention, a diagnosis value of the region of interest may be extracted and displayed to increase a diagnostic efficiency of an ultrasound apparatus for the user. In other words, according to an embodiment of the present invention, a plurality of different types of images with respect to the region of interest of an object may be displayed and thus, the user may use the displayed plurality of different types of displayed images to perform an overall diagnosis of the region of interest in a fast and precise manner.

According to an embodiment of the present invention, a parameter that may be obtained in different modes of the same area of the object (for example, the region of interest (ROI)) may be provided to enable an overall comparison and analysis of the ROI of the object. Also, a B mode image is obtained with priority and then images in various other modes may be obtained based on the ROI selected from the B mode image to simultaneously obtain and display various types of images used for diagnosis.

Figure 1:
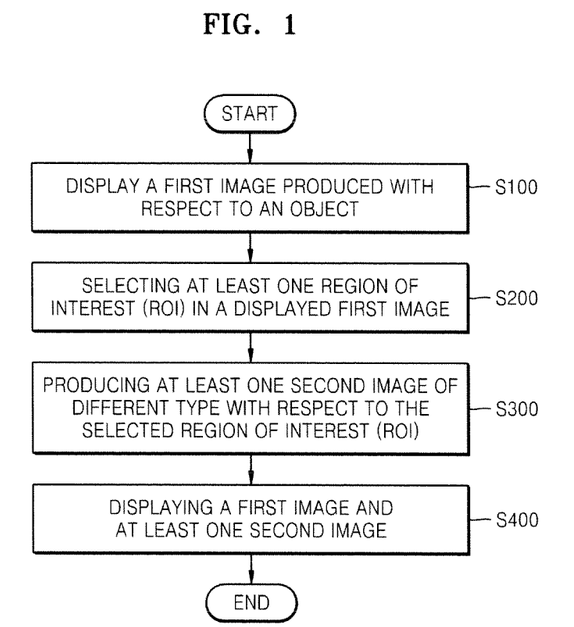
FIG. 1 is a flowchart of a method of displaying a plurality of different images of an object, according to an embodiment of the present invention.

FIG. 1 is a flowchart of a method of displaying a plurality of different images of an object according to an embodiment.

According to an embodiment of the present invention, a method of displaying a plurality of different images (of the object may include: displaying a first image produced with respect to an object S100; selecting at least one ROI from the displayed first image obtained therefrom S200; producing at least one second image of different type with respect to the selected at least one ROI S300; and displaying the first image and at least one second image S400. Each process will be described with reference to FIGS. 2A and 2B.

The first image according to an embodiment of the present invention may include a B mode image and the second image may include a functional image or a parametric image of the object. The functional image or the parametric image according to an embodiment of the present invention may include a color flow image, a shear modulus image, an attenuation image, an effective scatterer size map image, and a sound velocity map image.

The color flow image according to an embodiment of the present invention may include an image in which a frequency shift of a radio frequency (RF) echo reflected from a pulse of ultrasound irradiated to the object is used to calculate a velocity of a moving object, and calculation results obtained therefrom are expressed in predetermined colors.

Also, the shear modulus image may include an image expressed by using acoustic force that is relatively and strongly focused to generate a shear wave in tissue of the object and calculating a velocity of movements of the shear wave generated therefrom in the object to calculate a shear modulus of the object.

Also, the attenuation image may include an image generated based on the attenuation coefficients calculated using variations of RF echoes over a depth, knowing backscattering properties in the ROI of the object beforehand or assuming that the same does not change in the ROI. The variations in the RF echo signal may be determined by analyzing changes in a frequency or a magnitude of the RF echo signal.

Also, regarding the effective scatterer size map image, when the attenuation of the RF echo signal is compensated for, an inherent backscattering (a signal at an angle of 180° received from an object) function of the ROI may be obtained, and the effective scatterer size map image may include an image that displays sizes of effective scatterer obtained using a form factor that determines a shape of a scatterer. The size of the scatterer obtained therefrom may not an actual physical size and thus, it may be referred to as the effective scatterer size.

Also, the sound velocity map image may include an image showing sound velocity obtained on the basis of the fact that an image is well-focused and looks clear when the sound velocity used in the beamformer of the ultrasound apparatus matches that of the object.

Also, according to another embodiment of the present invention, the second image may include a functional image or a parametric image produced beforehand and stored in a storage unit (not shown), of the object. For example, when pre-acquired images are compared for tracing expression results of a lesion, the second image may include the functional image or the parametric image produced beforehand and stored in the storage unit (not shown), of the object, and a functional image or a parametric image produced during current diagnosis.

According to an embodiment of the present invention, the type of the second image may be preset or determined in real-time based on a frequency of use of each image, reliability of each image during diagnosis of a lesion, or external input. For example, when the object is breast, an image showing at least one of attenuation, sound velocity, shear wave velocity, and power doppler may be used in addition to the B mode image to aid in diagnosing a lesion within the breast in a fast and precise manner. In other words, comparing and analyzing plurality of the attenuation image, the sound velocity image, the shear wave velocity image, and the power doppler image by simultaneously displaying the same may help to determine the malignancy of the mass within the breast in a fast and precise manner.

The second image may have a varying frequency of use for each type of image depending on the type of examination (for example, cardiac function diagnosis, abdominal diagnosis, and fetal diagnosis) and thus, an image having high frequency of use may be produced with a high priority. For example, to determine the presence or absence of tumor in a breast, the shear wave velocity image may have high frequency of use. Accordingly, when determining the malignancy of a tumor within a breast, the apparatus may be preset to generate a shear wave velocity image. Also, to diagnose a lesion in the object, the user may enter the type of the second image that will be generated by using an external input, such that the second image may be modified in real-time through addition or deletion, depending on the type of image to be used.

Also, when the object is a breast as described above, the type of the second image to be produced may be determined based on the reliability of that image in diagnosis of a lesion. For example, in case of a breast mass, at least one image of an attenuation image, a sound velocity image, a shear wave velocity image, and a power doppler image, which are believed to have useful diagnostic values, may be set to be produced beforehand or in real-time.

Also, according to an embodiment of the present invention, a sequence of displaying at least one second image to be displayed with the first image may be preset or determined in real-time based on a frequency of use of each image, reliability during the diagnosis of a lesion, or an external input.

As described above, to determine the malignancy of a tumor in the breast, the shear wave velocity image may be utilized frequently thus, the shear wave velocity image may not only be generated during the diagnosis of a tumor in the breast, but also the generated shear wave velocity image may be displayed before another type of the second image (for example, a power doppler image or the like).

Also, a display sequence of the second image may be determined based on the reliability during the diagnosis of a lesion, and for example, for a breast examination, the second image may be displayed in a sequence of the shear wave velocity image, the power doppler image, the attenuation image, and the sound velocity image.

Also, the sequence for displaying the second image may be changed according to the external input entered by the user.

Figure 2A:
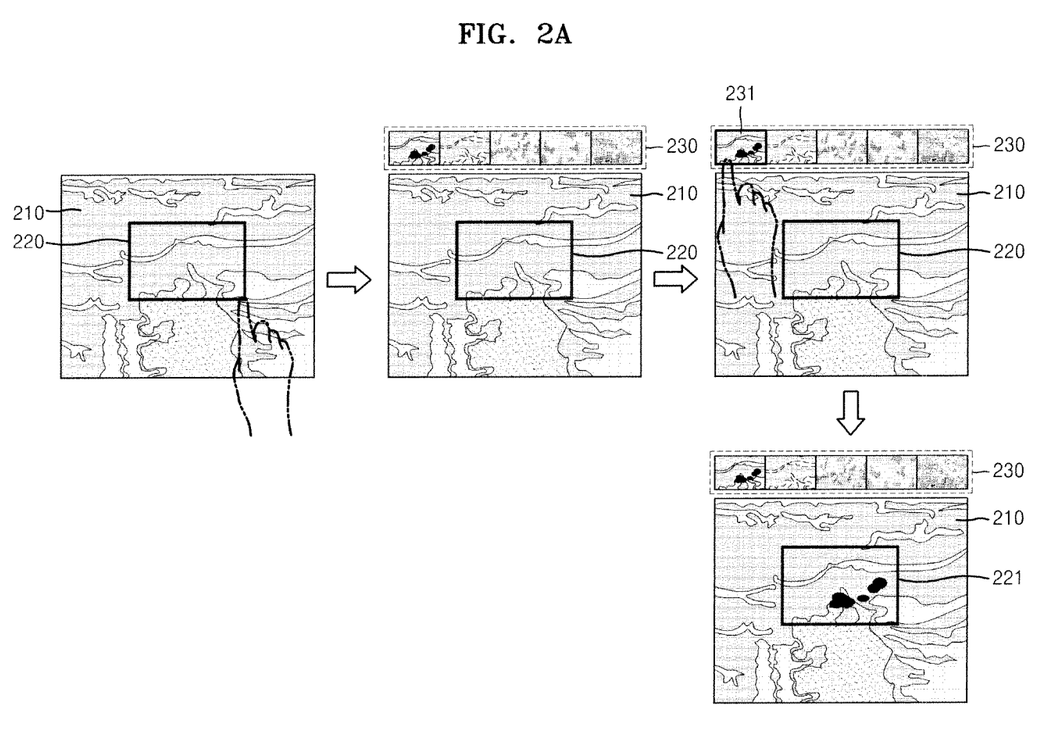
FIGS. 2A and 2B show a display of a plurality of different images of an object according to an embodiment of the present invention.
Figure 2B:
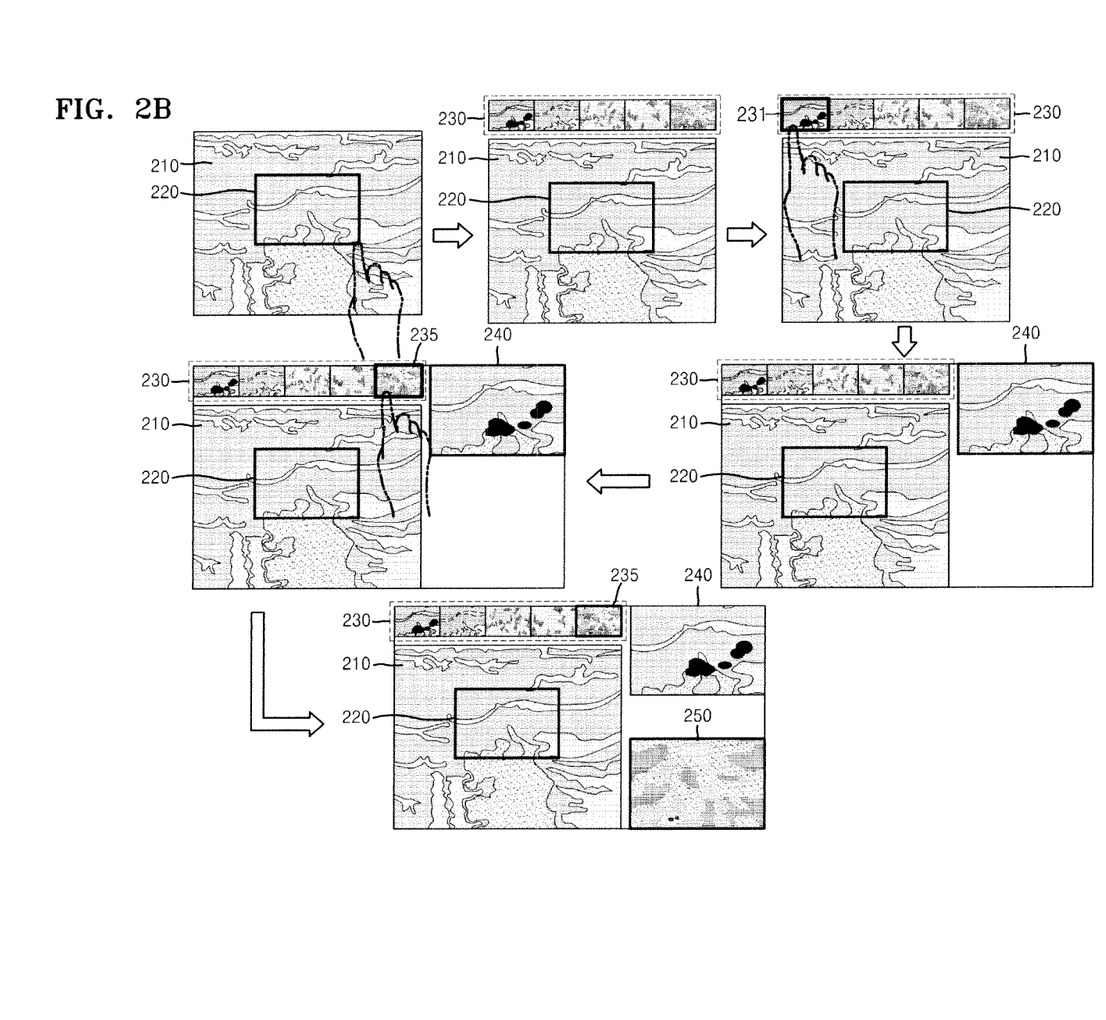

FIGS. 2A and 2B show a display of a plurality of different images of an object according to an embodiment.

Referring to FIG. 1 and according to an embodiment, a first image 210 generated with respect to the object may be displayed S100. As described above, the first image 210 may be a B mode image.

Also, at least one ROI 220 may be selected in the displayed first image 210 S200. The ROI 220 may be a predetermined region selected according to an external input or selected to have a predetermined area by the user. Also, the ROI 220 may be automatically generated according to a predetermined area including a boundary at which brightness changes abruptly in the first image 210 (for example, lesion or the like).

According to an embodiment of the present invention, with respect to the ROI 220, a second image set 230 including at least one type of second image may be generated S300. Also, the second image set 230 may be a set in which at least one of the produced second image is either simplified or reduced, or an identifier (includes letters, numbers, and icons) is set representing the second image. For example, an icon representing a power doppler image (PDI) may be generated as the second image set 230.

As described above, the second image may be a functional image or a parametric image. For example, the second image may include the attenuation image, the sound velocity image, the shear wave velocity image, and the PDI.

According to an embodiment, the first image 210 and the second image set 230 may be displayed S400. According to an embodiment, displaying the first image and at least one second image of the second image set 230 S400 may further include overlaying a second image selected according to an external input for selecting a second image from the second image set on the ROI to display. In other words, as shown in FIG. 2A, at least one image 231 may be selected from the produced second image set 230, such that the selected image 231 may be overlaid on the ROI 220 for a display 221.

Also, according to an embodiment of the present invention, displaying the first image 210 and at least one second image S400 may further include displaying the second image next to the first image 210 in parallel. As shown in FIG. 2B, the second image selected according to the external input for selecting the second image 231 from the second image set 230 may be displayed 240 in parallel next to the first image 210. The expression, "displayed in parallel" may refer to a display in a predetermined direction. The expression, "predetermined direction" may include at least one of up, down, left, right, and diagonal directions.

Also, the second image selected according to the external input for selecting a second image 235 from the second image set 230 may be displayed 250 next to the first image 210 to be displayed in parallel 250. Each of the selected second images 231 or 235 may be displayed 240 and 250 in a predetermined direction. As described above, the predetermined direction may include at least one of up, down, left, right, and diagonal directions.

Also, according to an embodiment of the present invention, the second image may be displayed according to a sequence of display that is determined as described above. For example, in the description above, the sequence of the shear wave velocity image, the PDI, the attenuation image, and the sound velocity image, which is in the order of high degree of association to the breast examination, may be, for example, sequentially displayed from the top (or left) to the bottom (or down) of a display unit.

Figure 3:
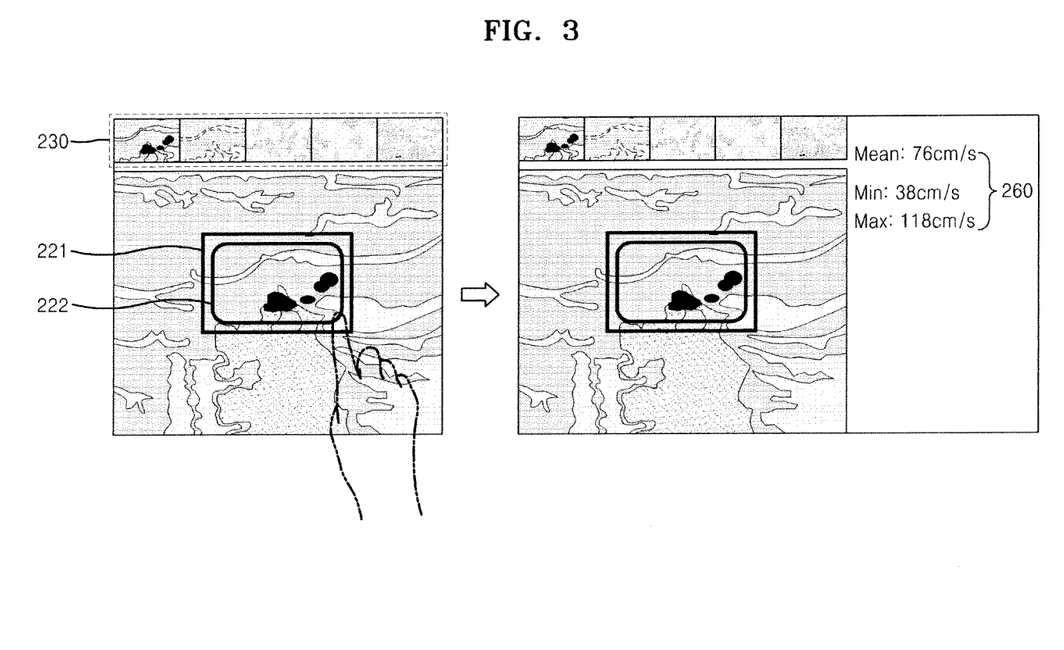
FIG. 3 shows a display of diagnosis values of an object according to an embodiment.

FIG. 3 shows a display of diagnosis values of the object according to an embodiment.

According to an embodiment of the present invention, the method may further include selecting at least one ROI from the displayed second image, extracting a predetermined diagnosis value from a selected sub-ROI, and displaying an extracted diagnosis value obtained therefrom.

Referring to FIGS. 2A and 3, at least one sub-ROI 222 may be selected from the second image that is displayed 221 to overlap the ROI 220. The sub-ROI 222 may have the same area in the same location as the ROI 220 of the first image or may be selected to have a smaller area than that of the ROI 220.

A predetermined diagnosis value may be extracted from data showing an image included in the selected sub-ROI 222. For example, the diagnosis value may include an average value, a median value, a standard deviation value, a minimum value, or a maximum value of a sound velocity, shear modulus, attenuation coefficient, and the like of movement of tissue or blood flow.

The extracted diagnosis value may be displayed through a display unit. For example, as shown in FIG. 3, the average value, the minimum value, and the maximum value of velocities of the movements of tissues or blood flow may be displayed as a diagnosis value 260. Accordingly, the user may determine the presence/absence of abnormalities in the object or the seriousness of a disease based on the diagnosis value provided.

Figure 4:
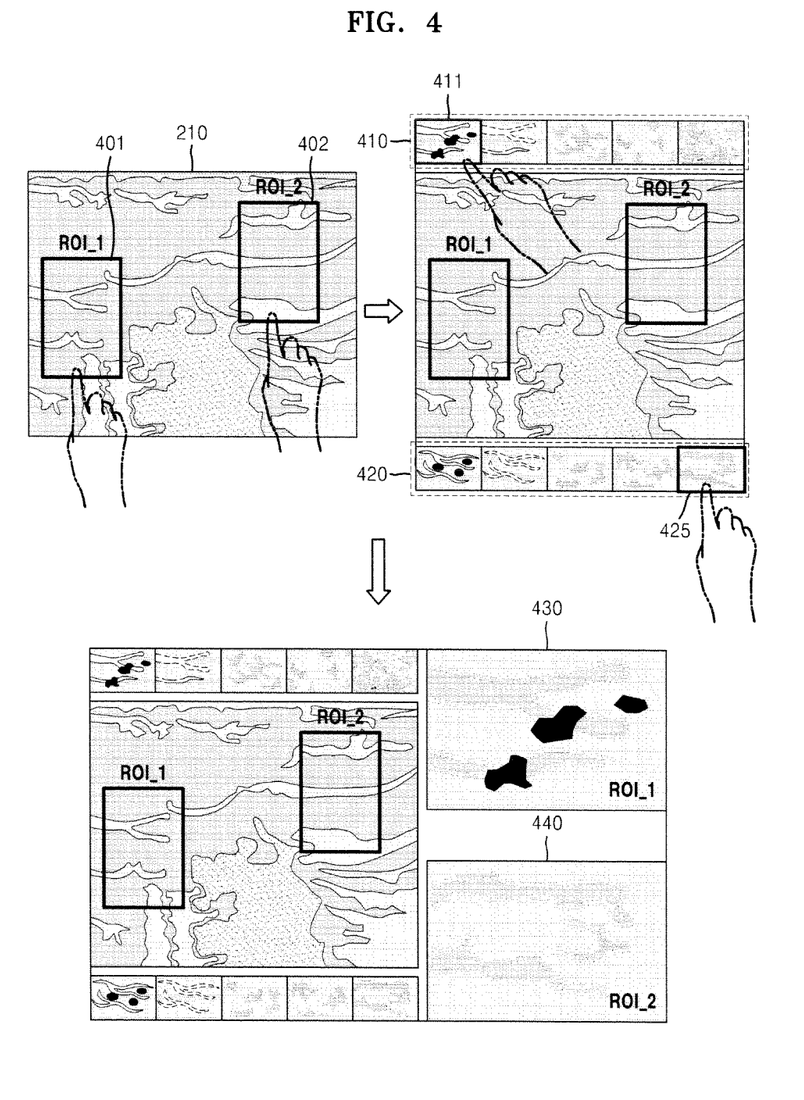
FIG. 4 shows a display of at least one type of image with respect to a plurality of selected regions of interest according to an embodiment of the present invention.

FIG. 4 shows a display of at least one type of image (with respect to a plurality of selected ROIs according to an embodiment of the present invention.

According to an embodiment of the present invention, when the plurality of ROIs, including a first ROI and a second ROI in a first image, are selected, a type of a second image produced with respect to the first ROI and a type of a second image produced with respect to the second ROI may be the same or different.

For example, as illustrated in FIG. 4, when the first ROI 401 and the second ROI 402 are selected, the type of the second image included in second image sets 410 and 420 produced for each ROI 401 or 402 may be the same or different. For example, a PDI, a shear wave velocity image, an attenuation image, and a sound velocity image, each of which may be included in the second image set 410 produced in correspondence to the first ROI 401 and the second image set 420 produced in correspondence to the second ROI 402. Also, a PDI, a shear wave velocity image, and an attenuation image may be included in the second image set 410 produced in correspondence to the first ROI 401, but only a PDI, an attenuation image, and a sound velocity image may be included in the second image set 420 produced in correspondence to the second ROI 402.

Referring to FIG. 2B and FIG. 4, a second image 411 selected in the second image set 410 produced in correspondence to the first ROI 401 may be disposed next to the first image 210 to be displayed 430 in parallel. Also, as shown in FIG. 2A, the image selected in the second image set 410 produced in correspondence to the first ROI 401 may overlap the first ROI 401 for a display. Likewise, a second image 425 selected in the second image set 420 produced in correspondence to the second ROI 402 may be disposed next to the first image 210 in parallel for a display 440. Also, as shown in FIG. 2A, the second image 425 selected in the second image set 420 produced in correspondence to the second ROI 402 may overlap the second ROI 402 for a display.

Figure 5:
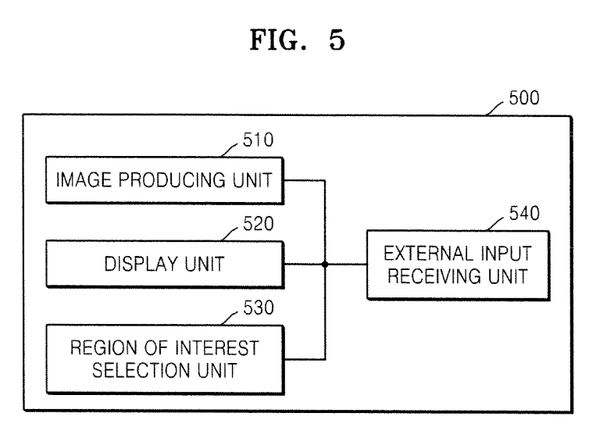
FIG. 5 is a block diagram of an apparatus displaying a plurality of different images of an object according to an embodiment of the present invention.

FIG. 5 is a block diagram of an apparatus 500 for displaying a plurality of different images of an object, according to an embodiment.

According to an embodiment of the present invention, provided is the apparatus 500 for displaying a plurality of different images of an object, the apparatus 500 including: an image producing unit 510 producing a first image of the object, a display unit 520 displaying the first image produced therefrom, and a ROI selection unit 530 selecting at least one ROI selected from at least one first image displayed therefrom. Also, the apparatus 500 according to an embodiment of the present invention may include an external input receiving unit 540 for receiving an external input. At least one of different types of the second image with respect to the selected ROI may be produced by the image producing unit 510. The first image and at least one second image may be displayed by the display unit 520.

The first image includes a B mode image and the second image may include a functional image or parametric image of the object.

A type of the second image may be preset or determined in real-time based on a frequency of use of each image, the reliability of each image in diagnosis of a lesion, or an external input.

A sequence of display of at least one second image to be displayed with the first image may be preset or determined in real-time based on a frequency of use of each image, the reliability in diagnosis of a lesion of each image, or an external input.

The display unit 52 may overlay the second image on the ROI according to an external input received through the external input receiving unit 540 to display the same or dispose the second image near the first image in parallel.

Figure 6:
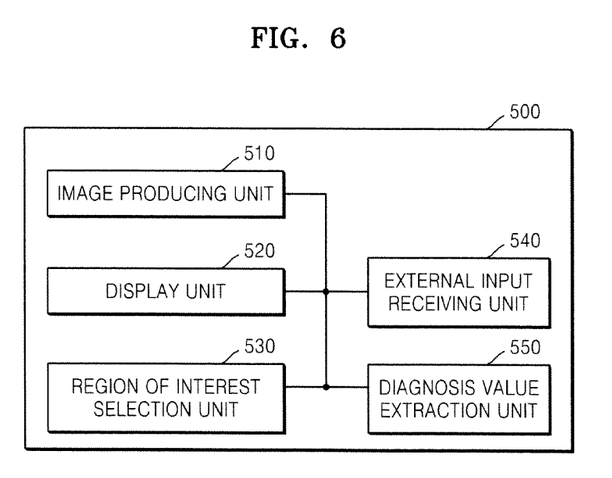
FIG. 6 is a block diagram of an apparatus displaying a plurality of different images of an object further including a diagnosis value extraction unit according to an embodiment of the present invention.

FIG. 6 is a block diagram of an apparatus 500 for displaying a plurality of different images of an object further including a diagnosis value extraction unit 550, according to an embodiment.

The apparatus 500 according to an embodiment of the present invention may further include the diagnosis value extraction unit 550 extracting a predetermined diagnosis value from a sub-ROI selected when at least one sub-ROI is selected in a displayed second image by a ROI selection unit 530. The extracted diagnosis value may be displayed by the display unit 520.

Also, when a plurality of ROIs including the first ROI and the second ROI are selected in the first image, a type of the second image produced for the first ROI and a type of the second ROI produced for the second ROI may be the same or different.

Descriptions about the method above may apply to the apparatus 500 and thus are not repeatedly provided In addition, other embodiments of the present invention can also be implemented through computer-readable code/instructions in/on a medium, e.g., a computer-readable medium, to control at least one processing element to implement any above-described embodiment. The medium can correspond to any medium/media permitting the storage and/or transmission of the computer-readable code.

The computer-readable code can be recorded/transferred on a medium in a variety of ways, with examples of the medium including recording media, such as magnetic storage media (e.g., ROM, floppy disks, hard disks, etc.) and optical recording media (e.g., CD-ROMs, DVDs, etc.), and transmission media such as Internet transmission media. Thus, the medium may be such a defined and measurable structure including or carrying a signal or information, such as a device carrying a bitstream according to one or more embodiments of the present invention. The media may also be a distributed network, so that the computer-readable code is stored/transferred and executed in a distributed fashion. Furthermore, the processing element could include a processor or a computer processor, and processing elements may be distributed and/or included in a single device.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A method of displaying a plurality of different images of an object, the method comprising:
displaying a first image produced with respect to the object;
selecting at least one region of interest from the displayed first image obtained therefrom;
producing a plurality of second images of a type different from a type of the first image, with respect to a selected region of interest;
displaying a second image set, which represents each of the plurality of second images, next to the first image;
selecting a second image from the second image set according to an external input; and
displaying the selected second image and the first image.

2. The method of claim 1, wherein
the first image comprises a B mode image, and
the plurality of second images comprises a functional image or a parametric image of the object.

3. The method of claim 1, wherein a type of the at least one plurality of second images is preset or determined in real-time based on a frequency of use of each image, reliability during a diagnosis of a lesion for each image, or an external input.

4. The method of claim 1, wherein a sequence of displaying the selected second image to be displayed with the first image is preset or determined in real-time based on a frequency of use of each image, reliability of each image during the diagnosis of a lesion, or an external input.

5. The method of claim 1, wherein displaying the first image and the selected second image further comprises overlaying the selected second image on the region of interest according to an external input to display the same or dispose the selected second image near the first image to be displayed in parallel.

6. The method of claim 1, wherein the method further comprises:
selecting at least one sub-region of interest from the displayed selected second image,
extracting a predetermined diagnosis value from a selected sub-region of interest obtained therefrom, and
displaying an extracted value obtained therefrom.

7. The method of claim 1, wherein when a plurality of regions of interest comprising a first region of interest (ROI) and a second region of interest (ROI) in the first image are selected, a type of a second image produced with respect to the first ROI and a type of a second image produced with respect to the second ROI are the same or different.

8. A non-transitory computer-readable recording medium, wherein a program for processing according to claim 1 is recorded.

9. An apparatus for displaying a plurality of different images of an object, the apparatus comprising:
an image producing unit producing a first image of the object,
a display unit displaying the first image produced therefrom, and
a region of interest selection unit selecting at least one region of interest selected from the first image displayed therefrom, wherein
the image producing unit produces a plurality of second images of a type different from a type of the first image, with respect to the selected region of interest,
the display unit displays a second image set, which represents each of the plurality of second images, next to the first image, and
the display unit displays a selected second image, which is selected from the second image set according to an external input, and the first image.

10. The apparatus of claim 9, wherein the first image comprises a B mode image and the plurality of second images comprises a functional image or a parametric image of the object.

11. The apparatus of claim 9, wherein a type of the plurality of second images is preset or determined in real-time based on a frequency of use of each image, reliability of each image in diagnosis of a lesion, or an external input.

12. The apparatus of claim 9, wherein a sequence of display of the selected second image to be displayed with the first image is preset or determined in real-time based on a frequency of use of each image, reliability of each image in diagnosis of a lesion, or an external input.

13. The apparatus of claim 9, wherein the display unit overlays the selected second image on the region of interest according to an external input to display the same or dispose the selected second image near the first image in parallel.

14. The apparatus of claim 9, the apparatus further comprising a diagnosis value extraction unit extracting a predetermined diagnosis value from a selected sub-region of interest when at least one sub-region of interest is selected in a displayed selected second image by a region of interest selection unit, wherein the diagnosis value extracted is displayed by the display unit.

15. The apparatus of claim 9, wherein when a plurality of regions of interest comprising a first region of interest and a second region of interest are selected in the first image, a type of a second image produced for the first region of interest and a type of a second image produced for the second region of interest are the same or different.

* * * * *